Figure 1:
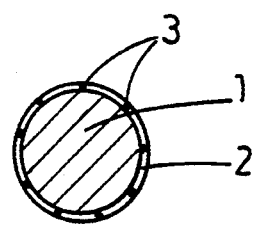

United States Patent [19]

Legro

[11] Patent Number: 5,389,115
[45] Date of Patent: Feb. 14, 1995

[54] PILLS OR PELLETS CONTAINING GENETIC MATERIAL AND INERT CARRIER MATERIAL AND METHOD FOR THEIR PREPARATION

[75] Inventor: Robert J. Legro, Enkhuizen, Netherlands

[73] Assignee: Incotec B.V., Enkhuizen, Netherlands

[21] Appl. No.: 977,775

[22] Filed: Nov. 17, 1992

[30] Foreign Application Priority Data

Nov. 21, 1991 [NL] Netherlands .......................... 9101959

[51] Int. Cl.$^6$ .......................... A01G 1/00; A01H 9/00; A01H 15/00
[52] U.S. Cl. ..................................... 47/57.6; 435/174; 435/176; 435/180
[58] Field of Search ............... 424/489; 435/174, 176, 435/177, 180, 181; 47/57.6; 71/64.01, 64.02, 64.04, DIG. 1

[56] References Cited

U.S. PATENT DOCUMENTS

| | | | |
|---|---|---|---|
| 2,736,139 | 2/1956 | Wise | 57/58.01 |
| 4,121,525 | 10/1978 | Courtis | 47/1.103 |
| 5,068,105 | 11/1991 | Lewis | 47/57.604 |

FOREIGN PATENT DOCUMENTS

0977178 11/1975 Canada .
2038316 2/1972 German Dem. Rep. .
0917736 4/1982 U.S.S.R. .

*Primary Examiner*—G. S. Kishore
*Attorney, Agent, or Firm*—D. Peter Hochberg; Mark Kusner; Michael Jaffe

[57] ABSTRACT

Pills or pellets containing genetic material and inert carrier material, characterized in that the inert carrier material forms the core of the pills or pellets, while the genetic material is distributed in a multitude around the core, adhering to that core in an adhesive layer and method for the preparation of pills or pellets containing genetic material and inert carrier material, characterized in that onto cores formed from inert carrier material a fluid adhesive containing genetic material is applied, if necessary diluted with other material, in a quantity corresponding with at least two genetic material units per present inert core, making up the adhesive layer, or that the genetic material is first mixed with a powdery adhesive, if necessary diluted with other powdery material in a quantity so that per present core at least two genetic material units are available, after which the mixture of genetic material and at least adhesive, and simultaneous addition of fluid to form the adhesive layer, is applied to the core, and finally, if desired, the layer is dried.

2 Claims, 1 Drawing Sheet

PILLS OR PELLETS CONTAINING GENETIC MATERIAL AND INERT CARRIER MATERIAL AND METHOD FOR THEIR PREPARATION

The invention relates to pills or pellets containing genetic material and inert carrier material and to a method for their preparation.

Such pills or pellets and the methods of their preparation are known, for instance, from the abstracts Seed Treatments, "Developments and Prospects", by A. A. Powell and S. Matthews, Outlook on Agriculture, vol. 17, No. 3, 1988 and Technical and Commercial Aspects of Seed Pelleting and Film Coating, by P. Halmer, Proceedings of a Symposium by the BCPC, 1988.

In the known methods for pill making or pelletizing the common essence is a target object, the seed, of which each individual part is covered, forming a pill or pellet, containing as core one seed only. For most seeds and markets this is desirable but for some it is not. Many flower seed pills could advantageously contain several seeds, but these cannot be covered by the existing methods.

Also, the existing methods are only suitable for making pills from or pelletizing relatively large seeds, as the pelletizing process is based on gravity. Covering small seeds individually meets with difficulties. In general the limit is a main dimension of 300 $\mu$m, with difficulties arising with seeds below 500 $\mu$m. Genetic material with dimensions in the order of 10-100 $\mu$m, such as for instance spores of ferns, fungi, for instance mushrooms and so on, cannot successfully be pelletized individually. Moreover, there is a definite need for several units of genetic material per seed unit.

Therefore there is a great demand for pills and pellets containing genetic material and inert carrier material, as well as a method for the preparation of these pills or pellets by which genetic material of small dimensions can also be pelletized and whereby the resulting pills may contain several seeds or spores.

Accordingly, the invention provides pills or pellets containing genetic material and inert carrier material, characterized in that the inert carrier material forms the core of the pills or pellets, while the genetic material is distributed in multiples around the core, adhering in an adhesive layer to that core.

The invention also comprises a method for the preparation of pills or pellets containing genetic material and inert carrier material, characterized in that a fluid adhesive containing genetic material, if necessary diluted with other material, in a quantity corresponding with at least two genetic material units per present inert core, making up the adhesive layer, is applied to cores formed from inert carrier material, or that the genetic material is first mixed with a powdery adhesive, if necessary diluted with other powdery material in a quantity so that per present core at least two genetic material units are available, after which the mixture of genetic material and at least adhesive, simultaneously adding fluid to form the adhesive layer, is applied to the core, and finally, if desired, the layer is dried.

It has been shown that such multi-seed pills, of which the core is formed from inert carrier material and the genetic material is distributed in a multitude around the inert core in an adhesive layer, allow good and more or less reproducible sowing of small genetic material such as fern spores, spores of fungi of 10-100 $\mu$m, as well as fine seed of 60-500 $\mu$m.

For the fluid adhesive one uses as a rule one of the usual adhesives known for pelletizing purposes, such as polymers which are dispersible or soluble in water, for instance polyvinyl alcohol, polyvinyl pyrrolidone, polyvinyl acetate, cellulose derivatives, as well as copolymers and related polymers.

As the solid powdery mixture one uses as a rule one of the usual fillers and binding materials known for pelletizing purposes, such as clay, cellulose powder, chalk, vermiculite, turf, perlite, talcum and quartz flour. If desired, fillers, pigments etc. may be added to the formulation of the adhesive layer.

According to the invention one departs from an inert core material, for instance glass beads or perlite granules. The cores may be individually provided with an adhesive layer, whereby, for instance, the spores are applied in a desired concentration by means of a solid or fluid formulation.

According to the invention one can also think of using a material for the inert core which, under the influence of fluid, swells and then disintegrates or collapses and dissolves, which causes optimal spreading of, for example, the spores in the cells of a seed tray.

If desired one can enclose in the adhesive layer or in the mixture of genetic material and adhesive an insecticide and/or fungicide, for the protection of the genetic material. Also, the physical and/or chemical properties of the adhesive layer can be determined such that optimal development, that is to say germination and growth of the target object, is achieved. This is called the microclimate. This can mean that the oxygen/water ratio is adjusted as well as the pH, and that pesticides, biostimulators or specific nutrients are added.

Characteristic for the invention is the presence per pill of at least 2 seeds, usually more than 5 seeds, increasing to several times ten (for example fern spores) or to hundreds to thousands (for example fungal spores, bacteria).

A BRIEF DESCRIPTION OF THE DRAWINGS

The invention is elucidated with reference to the accompanying drawing, in which:

FIG. 1 is an enlarged cross-section of a pill according to the invention;

FIG. 2 is an enlarged cross-section of a second embodiment;

FIG. 3 is an enlarged cross-section of a variation on the second embodiment; and FIG. 4 is an enlarged cross-section of a variation on the embodiment in FIG. 1.

The essence of the known coating system is that one departs from the seed as core, whereby the core material or the stationary phase consists in principle of the target object which finally is to expand. In general these cores are seeds. Around the core a layer is applied which, since it has to shape, could be called the mobile phase. This mobile phase may be fluid and then one speaks of a (film) coating process, which characteristically takes its course while simultaneously drying. The mobile phase can, however, also occur in powder form, whereby during simultaneous administration of fluid a layered build-up takes place until a pill or pellet has reached the desired size. This mobile phase is in principle free of genetic material and consists largely of inert carrier material, although active substances such as pesticides may be included.

In the multi-seed concept the principle is exactly reversed. As basis or stationary phase one departs from inert core material and the target object, essentially several units, are placed around the core via the mobile phase. This can be done in different ways, in one or more layers.

FIG. 1 shows a pill in cross-section whereby the genetic material 3 is applied in several units in a thin adhesive layer 2 around a core 1 of inert carrier material. This embodiment is very satisfactory if not much more needs to be added to the genetic material and/or if the material is to be applied in particular to the outside.

Figure 2:
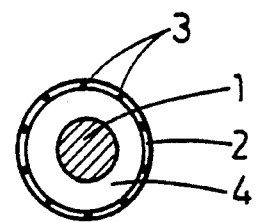

FIG. 2 shows another embodiment in cross-section, whereby first a somewhat thicker intermediate layer 4 is built up around a smaller core 1, which intermediate layer could be intended to include substances which may promote optimal development, germination and growth, in other words for the microclimate. Around the intermediate layer 4, which here determines the final size of the pill, a thin adhesive layer 2 is applied with a multitude of genetic material 3.

Figure 3:
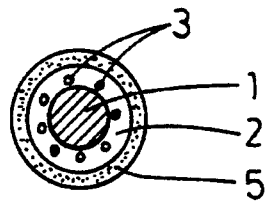

FIG. 3 shows another embodiment of the two-layer-type (FIG. 2), in which first a thicker adhesive layer 2 with filler is applied around the smaller core 1, with distributed over it the multitude of genetic material 3, and finally a coating 5 is applied over the whole. This coating may sometimes be necessary to give the pill a smooth finish.

Figure 4:
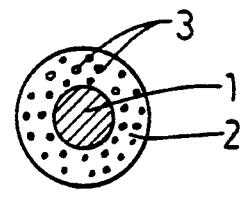

FIG. 4 shows a variation on the embodiment of FIG. 1. Here the core 1 is small, but the adhesive layer 2 is thick and suitable for inclusion of additives and of larger amounts of genetic material 3.

In all these cases the term "core 1" means the totally inert basic material, that is to say the stationary phase. The intermediate layer 4, consisting also essentially of carrier material, also mobile phase, is a layer that may optionally be applied underneath the final adhesive layer 2, which contains the target object (multitude of genetic material 3).

The adhesive layer 2 is also mobile phase and may be applied as solid or fluid form, but contains several units of the target object. The adhesive layer 5 is the mobile phase, applied for the finish and contains no target object.

The core material may be organic or inorganic, and of natural or synthetic origin. Examples are glass beads (solid as well as hollow), little plastic balls, selected perlite granules, selected granulates (possibly on sugar basis or on another water soluble basis, so that the core is completely dissolved in the ground), bentonite granulates that will dissolve with moisture, flowing away in the ground from the pill or pellet, and such like.

The basis of the adhesive layer, the optional intermediate layer and the optional coating layer will consist of the same substances that are used in conventional pelletizing and film coating. Examples of substances in the optional intermediate layer and in the adhesive layer are:

in the powdery basis: clay, cellulose powder, chalk, vermiculite, turf, perlite, talcum, quartz flour, and
in the fluid basis : water-dispersible or -soluble polymers such as polyvinyl alcohol, polyvinyl pyrrolidone, cellulose derivatives, copolymers and related polymers;

to the outside layer, which in many cases is the adhesive layer, pigments may be added if desired.

For the multi-seed concept there is no lower limit, but in practice the smallest workable dimension for, for example spores of different origin, will be around 10–60 $\mu$m. A defined upper limit is also difficult to indicate. The larger the target object becomes, the more difficult it will be for the concept to be carried out. The lower limit for conventional pelletizing (based on gravity) lies around 300 $\mu$m. The multi-seed concept is in any case still applicable for objects of up-to about 500 $\mu$m. Tests with lobelia seed of an average size of 575 $\mu$m and a thickness of 350 $\mu$m were reasonably successful (75% in the desired distribution).

The size of the core may vary between 0.5 and 3 mm in diameter, but must not be considered to be absolute. The size of the end-product may also vary a lot, depending on the intended purpose. Usually the final size will be between 1 mm round and 4 mm slot, which is the same as the usual seed pills. (The indications round and slot refer to the type of screen with which the size is measured.) The appearance of the pills is no different from the pills available according to the prior art so that they can also be sown using the existing sowing devices.

The invention is further elucidated with the aid of the following non-limitative examples.

EXAMPLE 1

Multi-seed fern spores

The size of the fern spores under consideration is about 50 $\mu$m. A dispersion is prepared of the fern spores in a watery solution of 3% polyvinyl alcohol, adjusting the concentration of the spores in the dispersion to the desired number per pill, in this particular case 20 spores per pill. The dispersion is acidified to the assumed optimal pH of 5.5–6.0.

In a fluid bed film coater, laboratory model, 50,000 plastic granules (because of low density these are easier to fluidize than, for instance, glass beads) being 2.5–3.0 mm round, are coated with the prepared dispersion of 20 spores per pill in the manner that is usual for seeds and dried simultaneously, whereby an adhesive layer is formed on the granules containing the spores in random distribution.

Example II

Multi-seed fern spores

The size of the fern spores is about 50 $\mu$m. From these spores a dry mixture is prepared with inert powder material consisting mainly of clay and quarts flour, whereby the concentration of the spores in the powder material is adjusted to the desired number per pill, in this particular example this is 20 spores per pill. The mixture is acidified to the assumed optimal pH of 5.5–6.0. (Measured after dilution with water).

100,000 glass granules being 0.75 mm round-1.00 mm slot, are placed in a coating drum with a diameter of 55 cm. As it is not desirable to end up with too large a glass granule, a relatively small glass granule and a two-phase coating was chosen, applying first, as intermediate layer, a carrier material around the relatively small core. This material will eventually dissolve into the ground. The carrier material used in this example again consists mainly of clay and quartz flour. The intermediate layer is applied until the dimension reaches from 1.75–2.00 mm slot.

Lastly, the final adhesive layer with the spores is applied on-to the intermediate layer, realizing a final dimension of 2.25–2.50 mm slot. Both the intermediate layer and the adhesive layer are applied while simultaneously a liquid spray on a water basis containing 5% polyvinyl alcohol is applied. Finally the multi-seed pills are dried by the method that is usual for drying seed pills. The coating process is not essentially different from the conventional coating process.

Example III

Multi-seed lobelia seeds

Lobelia seeds are about 600 μm long and about 300 μm thick. The seeds are mixed in the desired concentration with an inert powder material mixture consisting mainly of clay, quartz flour and coarse fibre whereby the differently sized granules are distributed so as to keep separation of the relatively large seeds during the process to a minimum. The concentration of the seeds in the mixture is adjusted to 5–10 seeds per pill.

100,000 selected perlite granules having a diameter of 1.50–1.75 mm slot, are placed in a coating drum with a diameter of 55 cm. The rough surface of the perlite granules forms a good basis for adhesion for the coarse mixture. With the aid of a watery solution of 5% carboxymethyl cellulose a thick adhesive layer is applied while alternating moistening with sprinkling the powdery mixture (in the same way as with the conventional coating system).

The pill is further smoothly finished with the aid of an inert powder mixture consisting mainly of clay, quarts flour and talcum, realizing a final size of 3.0–3.5 mm slot. Finally the multi-seed pills are dried by the method that is usual for drying seed pills.

Example IV

Multi-seed fungal! spores

The size of the fungal spores is about 15–35 μm. The spores are mixed in the desired concentration with an inert powder material mixture consisting mainly of clay, wood flour and quartz flour. The concentration of the fungal spores in the mixture is adjusted to about 3000 spores per pill.

100,000 glass granules having a diameter of 0.75 mm round-1.00 mm slot, are placed in a coating drum with a diameter of 55 cm. A thick adhesive layer is then applied around the glass granules by alternating moistening with a liquid spray consisting of a 10% polyvinyl acetate in water and sprinkling on the mixture, realizing a final size of 3.0–3.5 mm slot. Dependent on utilization the multi-seed pills may be left moist (limited storage time at a low temperature) or be partly or totally dried for ultimate use.

I claim:

1. A plurality of pills or pellets containing a multitude of spores selected from the group consisting of fern spores and fungi spores, and having a size of approximately 10–100 μm said spores are in or on an adhesive coating surrounding a core.

said core being inert with respect to said spores and is of material selected from the group consisting of glass beads, plastic beads, perlite granules, and/or bentonite granules, and having a diameter of between 5 mm and 2 mm.

2. A pill or pellet as defined in claim 1 and further comprising an outer coating encasing said adhseive coating, said coating is of a material from the group consisting of clay powder, quartz powder, flour, talcum powder, cellulose powder, vermiculite powder, and perlite powder.

* * * * *